United States Patent [19]
Prendergast et al.

[11] Patent Number: 5,605,830
[45] Date of Patent: Feb. 25, 1997

[54] MURINE AND HUMAN C-MYC INTERACTING PROTEIN

[75] Inventors: George C. Prendergast, Doylestown; Daitoku Sakamuro, Philadelphia, both of Pa.

[73] Assignee: The Wistar Institute of Anatomy & Biology, Philadelphia, Pa.

[21] Appl. No.: 435,454

[22] Filed: May 5, 1995

[51] Int. Cl.$^6$ .......................... C07H 21/04; C12N 15/85; C12N 15/63; C12N 15/12
[52] U.S. Cl. .............................. 435/325; 435/6; 435/69.1; 435/172.3; 435/252.33; 435/320.1; 435/348; 435/357; 435/358; 435/365; 435/366; 536/23.1; 536/23.5
[58] Field of Search ............................ 435/6, 69.1, 172.3, 435/240.1, 240.2, 252.33, 320.1; 536/23.1, 23.5; 514/44

[56] References Cited

U.S. PATENT DOCUMENTS 4,419,446 12/1983 Howley et al. ........................ 435/69.1

FOREIGN PATENT DOCUMENTS

WO91/18088 11/1991 WIPO .

OTHER PUBLICATIONS

Hillier, L., et al. The Washington–Merck EST Project. Apr. 14, 1995 Via MPSRCH Accesion# R18250.
Genexpress, Direct Submission 29–Jul.–1993 Via MPSRCH Accesion# 224784.
D. Negorev et al, "The Binl Gene Localizes to Human Chromosome 2q14 by PCR Analysis of Somatic Cell Hybrids and Fluorescence in Situ Hybridization", Genomics 33:329–331 (Apr. 1996).
Databases EMBL/Genebank/DDBJ on MPSRCH, Accession No. Z24792, Auffray et al, (Jul. 30, 1993).
Database Genexpress on MPSRCH, Accession No. Z28487, Auffray et al, (Dec., 1993).
Databases EMBL/GeneBank/DDBJ on MPSRCH, Accession No. F00405, Auffray et al, (Mar. 7, 1995).
Database IMAGE Consortium, LLNL on MPSRCH, Accession No. R34418, Hillier et al, (May 2, 1995).
M. Cole, "The myc Oncogene: Its Role in Transformation and Differentiation", Ann. Rev. Genet., 20:361–384 (1986).
D. Askew et al, "Constitutive c–myc Expression in an I1–3–dependent Myeloid Cell Line Suppresses Cell Cycle Arrest and Accelerates Apoptosis", Oncogene, 6:1915–1922 (Oct., 1991).
G. Evan et al, "Induction of Apoptosis in Fibroblasts by c–myc Protein", Cell, 69:119–128 (Apr. 3, 1992).
D. Sheiness et al, "Identification of Nucleotide Sequences which May Encode the Oncogenic Capacity of Avian Retrovirus MC29", J. Virol., 28(2) :600–610 (Nov., 1978).
T. Strohmeyer et al, "Review Article—Proto–Oncogenes and Tumor Suppressor Genes in Human Urological Malignancies", J. Urol., 151:1479–1497 (Jun., 1994).

M–J. Gething et al, "Cell–surface Expression of Influenza Haemagglutinin from a Cloned DNA Copy of the RNA Gene", Nature, 293:620–625 (Oct. 22, 1981).
R. Kaufman et al, "Coamplification and Coexpression of Human Tissue–Type Plasminogen Activator and Murine Dihydrofolate Reductase Sequences in Chinese Hamster Ovary Cells", Mol. Cell. Biol., 5(7):1750–1759 (Jul., 1985).
M. Kay et al, "In vivo Hepatic Gene Therapy: Complete Albeit Transient Correction of Factor IX Deficiency in Hemophilia B Dogs", Proc. Natl. Acad. Sci. USA, 91:2353–2357 (Mar., 1994).
S. Ishibashi et al, "Hypercholesterolemia in Low Density Lipoprotein Receptor Knockout Mice and its Reversal by Adenovirus–mediated Gene Delivery", J. Clin. Invest., 92:883–893 (Aug., 1993).
W. Huse et al, "Research Article—Generation of a Large Combinatorial Library of the Immunoglobuline Repertoire in Phage Lambda", Science, 246:1275–1281 (Dec. 8, 1989).
G. Mark et al, "Humanization of Monoclonal Antibodies", Chapter 4, The Handbook of Experimental Pharmacology, vol. 113, The Pharmacology of Monoclonal Antibodies, Springer–Verlag (Jun., 1994).
S. Fields et al, "A Novel Genetic System to Detect Protein–Protein Interactions", Nature, 340:245–246 (Jul. 20, 1989).
A. Vojtek et al, "Mammalian Ras Interacts Directly with the Serine/Threonine Kinase Raf", Cell, 74:205–214 (Jul. 16, 1993).
G. Prendergast et al, "A New Bind for Myc", Trends in Genet., 8(3) :91–97 (Mar., 1992) [Prendergast I].
A. Rustgi et al, "Amino–terminal Domains of c–myc and N–myc Proteins Mediate Binding to the Retinoblastoma Gene Product", Nature, 352:541–544 (Aug., 1991).
G. Prendergast et al, "Biphasic Effect of Max on Myc Cotransformation Activity and Dependence on Amino–and Carboxy–terminal Max Functions", Genes Dev., 6:2429–2439 (Dec., 1992) [Prendergast II].
A. Kelekar et al, "Immortalization by c–myc, H–ras, and Ela Oncogenes Induces Differential Cellular Gene Expression and Growth Factor Responses", Mol. Cell. Biol., 7(11) :3899–3907 (Nov., 1987).
C. Shih et al, "Isolation of a Transforming Sequence from a Human Bladder Carcinoma Cell Line", Cell, 29:161–169 (May, 1982).
E. Douglass et al, "A Specific Chromosomal Abnormality in Rhabdosarcoma", Cytogenet. Cell Genet., 45:148–155 (1987).
G. Prendergast et al, "Posttranscriptional Regulation of Cellular Gene Expression by the c–myc Oncogene", Mol. Cell. Biol., 9(1) :124–134 (Jan., 1989) [Prendergast III].

(List continued on next page.)

Primary Examiner—John L. LeGuyader
Assistant Examiner—Sean McGarry
Attorney, Agent, or Firm—Howson and Howson

[57] ABSTRACT

A partial murine cDNA clone and a human cDNA clone, each encoding a c-Myc interacting polypeptide termed MIP-99, are provided. Also provided are methods of using the nucleic acid sequences, polypeptides, and antibodies directed against same in the diagnosis and treatment of cancers and hyperplastic disease states.

8 Claims, 4 Drawing Sheets

OTHER PUBLICATIONS

F. Bauer et al, "Alteration of a Yeast SH3 Protein Leads to Conditional Viability with Defects in Cytoskeletal and Budding Patterns", *Mol. Cell. Biol.*, 13(8) :5070–5084 (Aug., 1993).

B. Lichte et al, "Amphiphysin, a Novel Protein Associated with Synaptic Vesicles", *EMBO J.*, 11(7) :2521–2530 (1992).

C. David et al, "Autoimmunity in Stiff–Man Syndrome with Breast Cancer is Targeted to the C–terminal Region of Human Amphiphysin, a Protein Similar to the Yeast Proteins, Rvs167 and Rvs161", *FEBS Letters*, 351:73–79 (Jul., 1994).

D. Miller et al, "An Insect Baculovirus Host–Vector System for High–Level Expression of Foreign Genes", *Genetic Engineering*, 8:277–298 (1986).

FIGURE 1

Partial Mouse MIP99 cDNA and Polypeptide
SEQ ID NOS. 1 and 2

| | | | | | | | | | | | | | | |
|---|---|---|---|---|---|---|---|---|---|---|---|---|---|---|
| GAG | ATC | AGA | GTG | AAC | CAT | GAG | CCA | GAG | CCG | GCC | AGT | GGG | GCC | TCA | 45
| Glu | Ile | Arg | Val | Asn | His | Glu | Pro | Glu | Pro | Ala | Ser | Gly | Ala | Ser |
| 1 | | | | 5 | | | | | 10 | | | | | 15 |

| CCC | GGG | GCT | GCC | ATC | CCC | AAG | TCC | CCA | TCT | CAG | CCA | GCA | GAG | GCC | 90
|---|---|---|---|---|---|---|---|---|---|---|---|---|---|---|
| Pro | Gly | Ala | Ala | Ile | Pro | Lys | Ser | Pro | Ser | Gln | Pro | Ala | Glu | Ala |
| | | | | 20 | | | | | 25 | | | | | 30 |

| TCC | GAG | GTG | GTG | GGT | GGA | GCC | CAG | GAG | CCA | GGG | GAG | ACA | GCA | GCC | 135
|---|---|---|---|---|---|---|---|---|---|---|---|---|---|---|
| Ser | Glu | Val | Val | Gly | Gly | Ala | Gln | Glu | Pro | Gly | Glu | Thr | Ala | Ala |
| | | | | 35 | | | | | 40 | | | | | 45 |

| AGT | GAA | GCA | ACC | TCC | AGC | TCT | CTT | CCG | GCT | GTG | GTG | GTG | GAG | ACC | 180
|---|---|---|---|---|---|---|---|---|---|---|---|---|---|---|
| Ser | Glu | Ala | Thr | Ser | Ser | Ser | Leu | Pro | Ala | Val | Val | Val | Glu | Thr |
| | | | | 50 | | | | | 55 | | | | | 60 |

| TTC | TCC | GCA | ACT | GTG | AAT | GGG | GCG | GTG | GAG | GGC | AGC | GCT | GGG | ACT | 225
|---|---|---|---|---|---|---|---|---|---|---|---|---|---|---|
| Phe | Ser | Ala | Thr | Val | Asn | Gly | Ala | Val | Glu | Gly | Ser | Ala | Gly | Thr |
| | | | | 65 | | | | | 70 | | | | | 75 |

| GGA | CGC | TTG | GAC | CTG | CCC | CCG | GGA | TTC | ATG | TTC | AAG | GTT | CAA | GCC | 270
|---|---|---|---|---|---|---|---|---|---|---|---|---|---|---|
| Gly | Arg | Leu | Asp | Leu | Pro | Pro | Gly | Phe | Met | Phe | Lys | Val | Gln | Ala |
| | | | | 80 | | | | | 85 | | | | | 90 |

| CAG | CAT | GAT | TAC | ACG | GCC | ACT | GAC | ACT | GAT | GAG | CTG | CAA | CTC | AAA | 315
|---|---|---|---|---|---|---|---|---|---|---|---|---|---|---|
| Gln | His | Asp | Tyr | Thr | Ala | Thr | Asp | Thr | Asp | Glu | Leu | Gln | Leu | Lys |
| | | | | 95 | | | | | 100 | | | | | 105 |

| GCT | GGC | GAT | GTG | GTG | TTG | GTG | ATT | CCT | TTC | CAG | AAC | CCA | GAG | GAG | 360
|---|---|---|---|---|---|---|---|---|---|---|---|---|---|---|
| Ala | Gly | Asp | Val | Val | Leu | Val | Ile | Pro | Phe | Gln | Asn | Pro | Glu | Glu |
| | | | | 110 | | | | | 115 | | | | | 120 |

| CAG | GAT | GAA | GGC | TGG | CTC | ATG | GGT | GTG | AAG | GAG | AGC | GAC | TGA | | 402
|---|---|---|---|---|---|---|---|---|---|---|---|---|---|---|
| Gln | Asp | Glu | Gly | Trp | Leu | Met | Gly | Val | Lys | Glu | Ser | Asp | | |
| | | | | 125 | | | | | 130 | | | | | |

FIGURE 2A

Human MIP99 cDNA and Polypeptide
SEQ ID NOS. 3 and 4

```
GAATTCCGTG CTGGTTGAGC TTGCTCATCT CCTTGTGGAA GTTTTCCTCC              50

AGGCCCGCG ATG CTC TGG AAC GTG GTG ACG GCG GGA AAG ATC GCC          95
           Met Leu Trp Asn Val Val Thr Ala Gly Lys Ile Ala
            1           5                        10

AGC AAC GTG CAG AAG AAG CTC ACC CGC GCG CAG GAG AAG GTT CTC       140
Ser Asn Val Gln Lys Lys Leu Thr Arg Ala Gln Glu Lys Val Leu
            15              20              25

CAG AAG CTG GGG AAG GCA GAT GAG ACC AAG GAT GAG CAG TTT GAG       185
Gln Lys Leu Gly Lys Ala Asp Glu Thr Lys Asp Glu Gln Phe Glu
            30              35              40

CAG TGC GTC CAG AAT TTC AAC AAG CAG CTG ACG GAG GGC ACC CGG       230
Gln Cys Val Gln Asn Phe Asn Lys Gln Leu Thr Glu Gly Thr Arg
            45              50              55

CTG CAG AAG GAT CTC CGG ACC TAC CTG GCC TCC GTC AAA GCC ATG       275
Leu Gln Lys Asp Leu Arg Thr Tyr Leu Ala Ser Val Lys Ala Met
            60              65              70

CAC GAG GCT TCC AAG AAG CTG AAT GAG TGT CTG CAG GAG GTG TAT       320
His Glu Ala Ser Lys Lys Leu Asn Glu Cys Leu Gln Glu Val Tyr
            75              80              85

GAG CCC GAT TGG CCC GGC AGG GAT GAG GCA AAC AAG ATC GCA GAG       365
Glu Pro Asp Trp Pro Gly Arg Asp Glu Ala Asn Lys Ile Ala Glu
            90              95             100

AAC AAC GAC CTG CTG TGG ATG GAT TAC CAC CAG AAG CTG GTG GAC       410
Asn Asn Asp Leu Leu Trp Met Asp Tyr His Gln Lys Leu Val Asp
            105             110             115

CAG GCG CTG CTG ACC ATG GAC ACG TAC CTG GGC CAG TTC CCC GAC       455
Gln Ala Leu Leu Thr Met Asp Thr Tyr Leu Gly Gln Phe Pro Asp
            120             125             130

ATC AAG TCA CGC ATT GCC AAG CGG GGG CGC AAG CTG GTG GAC TAC       500
Ile Lys Ser Arg Ile Ala Lys Arg Gly Arg Lys Leu Val Asp Tyr
            135             140             145

GAC AGT GCC CGG CAC CAC TAC GAG TCC CTT CAA ACT GCC AAA AAG       545
Asp Ser Ala Arg His His Tyr Glu Ser Leu Gln Thr Ala Lys Lys
            150             155             160
```

FIGURE 2B

```
AAG GAT GAA GCC AAA ATT GCC AAG GCC GAG GAG GAG CTC ATC AAA      590
Lys Asp Glu Ala Lys Ile Ala Lys Ala Glu Glu Glu Leu Ile Lys
        165             170                 175

GCC CAG AAG GTG TTT GAG GAG ATG AAT GTG GAT CTG CAG GAG GAG      635
Ala Gln Lys Val Phe Glu Glu Met Asn Val Asp Leu Gln Glu Glu
        180             185                 190

CTG CCG TCC CTG TGG AAC AGC CGC GTA GGT TTC TAC GTC AAC ACG      680
Leu Pro Ser Leu Trp Asn Ser Arg Val Gly Phe Tyr Val Asn Thr
        195             200                 205

TTC CAG AGC ATC GCG GGC CTG GAG GAA AAC TTC CAC AAG GAG ATG      725
Phe Gln Ser Ile Ala Gly Leu Glu Glu Asn Phe His Lys Glu Met
        210             215                 220

AGC AAG CTC AAC CAG AAC CTC AAT GAT GTG CTG GTC GGC CTG GAG      770
Ser Lys Leu Asn Gln Asn Leu Asn Asp Val Leu Val Gly Leu Glu
        225             230                 235

AAG CAA CAC GGG AGC AAC ACC TTC ACG GTC AAG GCC CAG CCC AGA      815
Lys Gln His Gly Ser Asn Thr Phe Thr Val Lys Ala Gln Pro Arg
        240             245                 250

AAG AAA AGT AAA CTG TTT TCG CGG CTG CGC AGA AAG AAG AAC AGT      860
Lys Lys Ser Lys Leu Phe Ser Arg Leu Arg Arg Lys Lys Asn Ser
        255             260                 265

GAC AAC GCG CCT GCA AAA GGG AAC AAG AGC CCT TCG CCT CCA GAT      905
Asp Asn Ala Pro Ala Lys Gly Asn Lys Ser Pro Ser Pro Pro Asp
        270             275                 280

GGC TCC CCT GCC GCC ACC CCC GAG ATC AGA GTC AAC CAC GAG CCA      950
Gly Ser Pro Ala Ala Thr Pro Glu Ile Arg Val Asn His Glu Pro
        285             290                 295

GAG CCG GCC GGC GGG GCC ACG CCC GGG GCC ACC CTC CCC AAG TCC      995
Glu Pro Ala Gly Gly Ala Thr Pro Gly Ala Thr Leu Pro Lys Ser
        300             305                 310

CCA TCT CAG CCA GCA GAG GCC TCG GAG GTG GCG GGT GGG ACC CAA     1040
Pro Ser Gln Pro Ala Glu Ala Ser Glu Val Ala Gly Gly Thr Gln
        315             320                 325

CCT GCG GCT GGA GCC CAG GAG CCA GGG GAG ACT TCT GCA AGT GAA     1085
Pro Ala Ala Gly Ala Gln Glu Pro Gly Glu Thr Ser Ala Ser Glu
        330             335                 340

GCA GCC TCC AGC TCT CTT CCT GCT GTC GTG GTG GAG ACC TTC CCA     1130
Ala Ala Ser Ser Ser Leu Pro Ala Val Val Val Glu Thr Phe Pro
        345             350                 355
```

FIGURE 2C

```
GCA ACT GTG AAT GGC ACC GTG GAG GGC GGC AGT GGG GCC GGG CGC    1175
Ala Thr Val Asn Gly Thr Val Glu Gly Gly Ser Gly Ala Gly Arg
        360             365                 370

TTG GAC CTG CCC CCA GGT TTC ATG TTC AAG GTA CAG GCC CAG CAC    1220
Leu Asp Leu Pro Pro Gly Phe Met Phe Lys Val Gln Ala Gln His
        375             380                 385

GAC TAC ACG GCC ACT GAC ACA GAC GAG CTG CAG CTC AAG GCT GGT    1265
Asp Tyr Thr Ala Thr Asp Thr Asp Glu Leu Gln Leu Lys Ala Gly
        390             395                 400

GAT GTG GTG CTG GTG ATC CCC TTC CAG AAC CCT GAA GAG CAG GAT    1310
Asp Val Val Leu Val Ile Pro Phe Gln Asn Pro Glu Glu Gln Asp
        405             410                 415

GAA GGC TGG CTC ATG GGC GTG AAG GAG AGC GAC TGG AAC CAG CAC    1355
Glu Gly Trp Leu Met Gly Val Lys Glu Ser Asp Trp Asn Gln His
        420             425                 430

AAG AAG CTG GAG AAG TGC CGT GGC GTC TTC CCC GAG AAC TTC ACT    1400
Lys Lys Leu Glu Lys Cys Arg Gly Val Phe Pro Glu Asn Phe Thr
        435             440                 445

GAG AGG GTC CCA TGACGGCGGG GCCCAGGCAG CCTCCGGGCG TGTGAAGAAC    1452
Glu Arg Val Pro
        450

ACCTCCTCCC GAAAAATGTG TGGTTCTTTT TTTTGTTTTG TTTTCGTTTT         1502

TCATCTTTTG AAGAGCAAAG GGAAATCAAG AGGAGACCCC CAGGCAGAGG         1552

GGCGTTCTCC CAAAGTTTAG GTCGTTTTCC AAAGAGCCGC GTCCCGGCAA         1602

GTCCGGCGGA ATTCACCAGT GTTCCTGAAG CTGCTGTGTC CTCTAGTTGA         1652

GTTTCTGGCG CCCCTGCCTG TGCCCGCATG TGTGCCTGGC CGCAGGGCGG         1702

GGCTGGGGGC TGCCGAGCCA CCATACTTAA CTGAAGCTTC GGCCGCACCA         1752

CCCGGGGAAG GGTCCTCTTT TCCTGGCAGC TGCTGTGGGT GGGGCCCAGA         1802

CACCAGCCTA GCCTGCTCTG CCCCGCAGAC GGTCTGTGTG CTGTTTGAAA         1852

ATAAATCTTA GTGTTCAAAA CAAAATGAAA CAAAAAAAAA AATGATAAAA         1902

ACTCTCAAAA AAACAAGGAA TTC                                      1925
```

MURINE AND HUMAN C-MYC INTERACTING PROTEIN

This invention was made with financial assistance from the National Institutes of Health Grant No. 5-P30-CA-10815-28. The United States government has certain rights in this invention.

FIELD OF THE INVENTION

This invention relates generally to cancer diagnosis and therapy, and more specifically, to cancers associated with the Myc oncoprotein.

BACKGROUND OF THE INVENTION

Myc is a transcription factor and key cell growth regulator that is frequently deregulated in human malignancy, notably Burkitt's and T cell lymphomas, where myc genes suffer chromosomal translocation. In colon and lung carcinomas, myc genes are amplified [M. D. Cole, Ann. Rev. Genet., 20:361–384 (1986)]. Paradoxically, under certain conditions myc can induce apoptosis [D. S. Askew et al, Oncogene, 6:1915–1922 (1991); G. I. Evan et al, Cell, 69:119–128 (1992)], a phenotype consistent with its original identification (and naming) as a retroviral gene that induces myelocytomatosis (myeloid cell death) as well as tumorigenesis [D. Sheiness et al, J. Virol., 28:600–610 (1978)]. Loss or suppression of apoptosis is an important step in the malignant conversion of human tumors containing deregulated myc oncogenes, including, prominently, prostate carcinoma [T. G. Strohmeyer et al, J. Urol., 151:1479–1497 (1994)].

There remains a need in the art for compositions and methods of regulating a deregulated Myc protein and/or diagnosing the occurrence of such deregulation.

BRIEF DESCRIPTION OF THE DRAWINGS

FIG. 1 is a partial murine cDNA sequence SEQ ID NO:1 and the murine MIP-99 polypeptide encoded thereby SEQ ID NO:2.

FIG. 2 is a human cDNA sequence SEQ ID NO:3 and the human MIP-99 polypeptide encoded thereby SEQ ID NO:4.

SUMMARY OF THE INVENTION

In one aspect, the present invention provides a partial murine cDNA clone of a c-Myc interacting protein (MIP), referred to as MIP-99, SEQ ID NO:1, and the polypeptide encoded thereby, SEQ ID NO:2.

In another aspect, the present invention provides a human MIP-99 cDNA clone, SEQ ID NO:3, and the human polypeptide encoded thereby, SEQ ID NO:4.

In yet another aspect, the present invention provides a vector comprising a mammalian nucleic acid sequence encoding a MIP-99 protein and a host cell transformed by such a vector. Alternatively, this vector may be used in gene therapy applications.

In still another aspect, the invention provides an oligonucleotide probe comprising a nucleic acid sequence as defined herein. Also provided is an antibody raised against a MIP-99 protein or peptide thereof.

In yet a further aspect, the present invention provides a diagnostic reagent for breast or liver cancer, or deficient MIP-99 production, comprising an oligonucleotide probe or an antibody of the invention.

Further provided is a therapeutic reagent comprising a polypeptide, anti-idiotype antibody, or gene therapy vector of the invention.

Still another aspect of the invention provides a method of treating breast or liver cancer by administering a therapeutic reagent of the invention.

Other aspects and advantages of the present invention are described further in the following detailed description of the preferred embodiments thereof.

DETAILED DESCRIPTION OF THE INVENTION

The present invention provides novel, isolated, nucleic acid sequences which encode novel proteins which interact with c-Myc and bind thereto, fragments of these sequences and antibodies developed thereto. The nucleic acid sequences, protein sequences and antibodies are useful in the detection, diagnosis and treatment of cancers or other disorders associated with deregulation, deficiency or amplification of the c-myc oncogenes. Further, when a c-Myc interacting protein or peptide (called MIP-99) of this invention binds to c-Myc, the binding appears to regulate the c-Myc and result in tumor suppression. Particularly, the MIP99 gene has several features suggesting it is a tumor suppressor gene. First, MIP99 inhibits Myc-dependent malignant cell transformation. Second, Southern analysis of the MIP99 gene reveals that it is mutated in a significant portion of human liver carcinoma cell lines. Third, Northern analysis indicates that expression of MIP99 RNA is lost in human liver and breast carcinoma cell lines. All of these features are characteristic of tumor suppressor genes including the breast cancer gene BRCA1, and the genes encoding p53 and the Rb retinoblastoma protein, which are negative regulators of cell growth that are observed to be mutated and/or unexpressed in human cancer cells. These aspects of the invention are discussed in more detail below.

I. Nucleic Acid Sequences

The present invention provides a mammalian nucleic acid sequence encoding a c-myc interacting peptide or protein, termed herein MIP-99. The nucleic acid sequences of this invention are isolated from cellular materials with which they are naturally associated. In one embodiment, a MIP-99 nucleic acid sequence is selected from all or part of the partial murine cDNA clone, SEQ ID NO:1. In another embodiment, a MIP-99 nucleic acid sequence is selected from all or part of a human cDNA clone, SEQ ID NO:3. However, the present invention is not limited to these nucleic acid sequences.

Given the sequences of SEQ ID NO:1 and SEQ ID NO:3, one of skill in the art can readily obtain the corresponding anti-sense strands of these cDNA sequences. Further, using known techniques, one of skill in the art can readily obtain the genomic sequences corresponding to these cDNA sequences or the corresponding RNA sequences, as desired.

Similarly the availability of SEQ ID NOS: 1 and 3 of this invention permits one of skill in the art to obtain other species MIP-99 analogs, by use of the nucleic acid sequences of this invention as probes in a conventional technique, e.g., polymerase chain reaction. Allelic variants of these sequences within a species (i.e., nucleotide sequences containing some individual nucleotide differences from a more commonly occurring sequence within a species, but which nevertheless encode the same protein) such as other human variants of MIP-99 SEQ ID NO:3, may also be readily obtained given the knowledge of this sequence provided by this invention.

The present invention further encompasses nucleic acid sequences capable of hybridizing under stringent conditions [see, J. Sambrook et al, *Molecular Cloning: A Laboratory Manual,* 2d ed., Cold Spring Harbor Laboratory (1989)] to the sequences of SEQ ID NO:1, SEQ ID NO:3, their anti-sense strands, or biologically active fragments thereof. An example of a highly stringent hybridization condition is hybridization at 2× SSC at 65° C., followed by a washing in 0.1× SSC at 65° C. for an hour. Alternatively, an exemplary highly stringent hybridization condition is in 50% formamide, 4× SSC at 42° C. Other, moderately high stringency conditions may also prove useful, e.g. hybridization in 4× SSC at 55° C., followed by washing in 0.1× SSC at 37° C. for an hour. Alternatively, an exemplary moderately high stringency hybridization condition is in 50% formamide, 4× SSC at 30° C.

Also encompassed within this invention are fragments of the above-identified nucleic acid sequences. Preferably, such fragments are characterized by encoding a biologically active portion of MIP-99, e.g., an epitope. Generally, these oligonucleotide fragments are at least 15 nucleotides in length. However, oligonucleotide fragments of varying sizes may be selected as desired. Such fragments may be used for such purposes as performing the PCR, e.g., on a biopsied tissue sample. Other uses of such fragments are discussed in more detail below.

The nucleotide sequences of the invention may be isolated by conventional uses of polymerase chain reaction or cloning techniques such as those described in obtaining the murine and human sequences, described below. Alternatively, these sequences may be constructed using conventional genetic engineering or chemical synthesis techniques.

According to the invention, the nucleic acid sequences [SEQ ID NO:1 and SEQ ID NO:3], may be modified. Utilizing the sequence data in these figures, it is within the skill of the art to obtain other polynucleotide sequences encoding the proteins of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are mutants of the MIP-99 gene provided herein. Such mutants include amino terminal, carboxy terminal or internal deletions which are useful as dominant inhibitor genes. Such a truncated, or deletion, mutant may be expressed for the purpose of inhibiting the activity of the full-length or wild-type gene. For example, it has been found that expression of the partial murine MIP99 provided herein [SEQ ID NO:2] acts to inhibit normal MIP99 activity. Expression of this protein is described in Example 3 below.

These nucleic acid sequences are useful for a variety of diagnostic and therapeutic uses. Advantageously, the nucleic acid sequences are useful in the development of diagnostic probes and antisense probes for use in the detection and diagnosis of conditions characterized by deregulation or amplification of c-myc. The nucleic acid sequences of this invention are also useful in the production of mammalian, and particularly, murine and human MIP-99 proteins.

II. Protein Sequences

The present invention also provides mammalian MIP-99 polypeptides or proteins. These proteins are free from association with other contaminating proteins or materials with which they are found in nature. In one embodiment, the invention provides a partial murine MIP-99 [SEQ ID NO:2] polypeptide of 135 amino acids having a predicted molecular weight (MW) of 13,688. In another embodiment, the invention provides a full-length human MIP-99 [SEQ ID NO:4] of 451 amino acids with an estimated MW of 50,048. The apparent MW of human MIP-99 on sodium dodecyl sulfate polyacrylamide (SDS-PA) gels is approximately 67 kD.

Further encompassed by this invention are fragments of the MIP-99 polypeptides. Such fragments are desirably characterized by having MIP-99 biological activity, including, e.g., the ability to interact with c-Myc. These fragments may be designed or obtained in any desired length, including as small as about 8 amino acids in length. Such a fragment may represent an epitope of the protein.

Also included in the invention are analogs, or modified versions, of the proteins provided herein. Typically, such analogs differ by only one to four codon changes. Examples include polypeptides with minor amino acid variations from the illustrated amino acid sequences of MIP-99 (FIGS. 1 and 2; SEQ ID NO:2 and 4); in particular, conservative amino acid replacements. Conservative replacements are those that take place within a family of amino acids that are related in their side chains and chemical properties. Also provided are homologs of the proteins of the invention which are characterized by having at least 85% homology with SEQ ID NO:2 or SEQ ID NO:4. It has previously determined that the murine and human MIP 99 (in partial) are about 88.5% identical.

Additionally, the MIP-99 proteins [SEQ ID NO:2 and 4] of the invention may be modified, for example, by truncation at the amino or carboxy termini, by elimination or substitution of one or more amino acids, or by any number of now conventional techniques to improve production thereof, to enhance protein stability or other characteristics, e.g. binding activity or bioavailability, or to confer some other desired property upon the protein. For example, Example 3 illustrates the ability of a truncated MIP-99 [SEQ ID NO:2] to inhibit normal MIP-99 activity III. Expression A. In Vitro To produce recombinant MIP-99 proteins of this invention, the DNA sequences of the invention are inserted into a suitable expression system. Desirably, a recombinant molecule or vector is constructed in which the polynucleotide sequence encoding MIP-99 is operably linked to a heterologous expression control sequence permitting expression of the murine or human MIP-99 protein. Numerous types of appropriate expression vectors are known in the art for mammalian (including human) protein expression, by standard molecular biology techniques. Such vectors may be selected from among conventional vector types including insects, e.g., baculovirus expression, or yeast, fungal, bacterial or viral expression systems. Other appropriate expression vectors, of which numerous types are known in the art, can also be used for this purpose.

Methods for obtaining such expression vectors are well-known. See, Sambrook et al, *Molecular Cloning. A Laboratory Manual,* 2d edition, Cold Spring Harbor Laboratory, N.Y. (1989); Miller et al, *Genetic Engineering,* 8:277–298 (Plenum Press 1986) and references cited therein.

Suitable host cells or cell lines for transfection by this method include mammalian cells, such as Human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, and product production and purification are known in the art. [See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446].

Similarly bacterial cells are useful as host cells for the present invention. For example, the various strains of *E. coli* (e.g., HB101, MC1061, and strains used in the following examples) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the polypeptides of the present invention. Other fungal cells may also be employed as expression systems.

Alternatively, insect cells such as *Spodoptera frugipedera* (Sf9) cells may be used.

Thus, the present invention provides a method for producing a recombinant MIP-99 protein which involves transfecting a host cell with at least one expression vector containing a recombinant polynucleotide encoding a MIP-99 protein under the control of a transcriptional regulatory sequence, e.g. by conventional means such as electroporation. The transfected host cell is then cultured under suitable conditions that allow expression of the MIP-99 protein. The expressed protein is then recovered, isolated, and optionally purified from the culture medium (or from the cell, if expressed intracellularly) by appropriate means known to one of skill in the art.

For example, the proteins may be isolated following cell lysis in soluble form, or may be extracted using known techniques, e.g., in guanidine chloride. If desired, the MIP-99 proteins of the invention may be produced as a fusion protein. For example, it may be desirable to produce MIP-99 fusion proteins, to enhance expression of the protein in a selected host cell, to improve purification, or for use in monitoring the presence of MIP99 in tissues, cells or cell extracts. Suitable fusion partners for the MIP-99 proteins of the invention are well known to those of skill in the art and include, among others, β-galactosidase, glutathione-S-transferase, and poly-histidine.

B. In Vivo

Alternatively, where it is desired that the MIP-99 protein be expressed in vivo, e.g., for gene therapy purposes, an appropriate vector for delivery of the MIP-99 protein, or fragment thereof, may be readily selected by one of skill in the art. Exemplary gene therapy vectors are readily available from a variety of academic and commercial sources, and include, e.g., adeno-associated virus [International patent application No. PCT/US91/03440], adenovirus vectors [M. Kay et al, *Proc. Natl. Acad. Sci. USA*, .91:2353 (1994); S. Ishibashi et al, *J. Clin. Invest.*, 92:883 (1993)], or other viral vectors, e.g., various poxviruses, vaccinia, etc. Methods for insertion of a desired gene, e.g. MIP-99, and obtaining in vivo expression of the encoded protein, are well known to those of skill in the art.

IV. Antisera and Antibodies

The MIP-99 proteins of this invention are also useful as antigens for the development of anti-MIP antisera and antibodies to MIP-99 or to a desired fragment of a MIP-99 protein. Specific antisera may be generated using known techniques. See, Sambrook, cited above, Chapter 18, generally, incorporated by reference. Similarly, antibodies of the invention, both polyclonal and monoclonal, may be produced by conventional methods, including the Kohler and Milstein hybridoma technique, recombinant techniques, such as described by Huse et al, *Science*, 246:1275–1281 (1988), or any other modifications thereof known to the art.

Also encompassed within this invention are humanized and chimeric antibodies. As used herein, a humanized antibody is defined as an antibody containing murine complementary determining regions (CDRs) capable of binding to MIP-99 or a fragment thereof, and human framework regions. These CDRs are preferably derived from a murine monoclonal antibody (MAb) of the invention. As defined herein, a chimeric antibody is defined as an antibody containing the variable region light and heavy chains, including both CDR and framework regions, from a MIP-99 MAb of the invention and the constant region light and heavy chains from a human antibody. Methods of identifying suitable human framework regions and modifying a MAb of the invention to contain same to produce a humanized or chimeric antibody of the invention, are well known to those of skill in the art. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994). Other types of recombinantly-designed antibodies are also encompassed by this invention.

Further provided by the present invention are anti-idiotype antibodies (Ab2) and anti-anti-idiotype antibodies (Ab3). Ab2 are specific for the target to which anti-MIP-99 antibodies of the invention bind and Ab3 are similar to MIP-99 antibodies (Ab1) in their binding specificities and biological activities [see, e.g., M. Wettendorff et al., "Modulation of anti-tumor immunity by anti-idiotypic antibodies." In *Idiotypic Network and Diseases*, ed. by J. Cerny and J. Hiernaux J, Am. Soc. Microbiol., Washington D.C.: pp. 203–229, (1990)].

These anti-idiotype and anti-anti idiotype antibodies may be produced using techniques well known to those of skill in the art. Such anti-idiotype antibodies (Ab2) can bear the internal image of the c-Myc and bind to it in much the same manner as MIP-99 and are thus useful for the same purposes as MIP-99.

In general, polyclonal antisera, monoclonal antibodies and other antibodies which bind to MIP-99 as the antigen (Ab1) are useful to identify epitopes of MIP-99, to separate MIP-99 from contaminants in living tissue (e.g., in chromatographic columns and the like), and in general as research tools and as starting material essential for the development of other types of antibodies described above. Anti-idiotype antibodies (Ab2) are useful for binding c-Myc and thus may be used in the treatment of cancers in which c-Myc is part of a biochemical cascade of events leading to tumor formation. The Ab3 antibodies may be useful for the same reason the Ab1 are useful. Other uses as research tools and as components for separation of c-Myc from other contaminant of living tissue, for example, are also contemplated for these antibodies.

V. Diagnostic Reagents and Methods

Advantageously, the present invention provides reagents and methods useful in detecting and diagnosing abnormal levels of MIP 99, and particularly deficiencies or excess production thereof, in a patient. As defined herein, a deficiency of MIP-99 is defined as an inadequate amount of MIP-99 to compensate for the levels of c-Myc in a patient. Conditions associated with deficiencies of MIP-99 include a variety of cancers, e.g., breast cancer, liver cancer and colon cancer, and hyperplastic disease states, e.g., benign prostate hyperplasia.

Thus, the proteins, antibodies, and polynucleotide sequences (including anti-sense polynucleotide sequences and oligonucleotide fragments), and MIP-99 anti-sera and antibodies of this invention may be useful as diagnostic reagents. These reagents may optionally be labelled using diagnostic labels, such as radioactive labels, colorimetric enzyme label systems and the like conventionally used in diagnostic or therapeutic methods. Alternatively, the N- or C-terminus of MIP99 or a fragment thereof may be tagged with a viral epitope which can be recognized by a specific antisera. The reagents may be used to measure abnormal MIP-99 levels in selected mammalian tissue in conventional diagnostic assays, e.g., Southern blotting, Northern and Western blotting, polymerase chain reaction (PCR), reverse transcriptase (RT) PCR, immunostaining, and the like. For example, in biopsies of tumor tissue, loss of MIP99 expression in tumor tissue could be directly verified by RT-PCR or immunostaining. Alternatively, a Southern analysis, genomic PCR, or fluorescence in situ hybridization (FISH) may be performed to confirm MIP99 gene rearrangement.

In one example, as diagnostic agents the polynucleotide sequences may be employed to detect or quantitate normal MIP-99. The selection of the appropriate assay format and label system is within the skill of the art and may readily be chosen without requiring additional explanation by resort to the wealth of art in the diagnostic area.

Thus the present invention provides methods for the use of these protein, antibody, antisera or polynucleotide reagents in the detection of disorders characterized by insufficient MIP-99 levels. The methods involve contacting a selected mammalian tissue, e.g., a biopsy sample or other cells, with the selected reagent, protein, antisera antibody or DNA sequence, and measuring or detecting the amount of MIP-99 present in the tissue in a selected assay format based on the binding or hybridization of the reagent to the tissue.

VI. Therapeutic Compositions and Methods

Compositions and methods useful for the treatment of conditions associated with inadequate MIP-99 levels are provided. As stated above, included among such conditions are liver, colon and breast cancers and hyperplastic disease states. Also provided are compositions and methods for inhibiting MIP-99 activity in order to ameliorate a condition in which apoptosis is activated and MIP99 plays a role. Such conditions may include degenerative conditions, e.g., neurodegenerative diseases.

The therapeutic compositions of the invention may be formulated to contain an anti-idiotype antibody of the invention, or the MIP-99 protein itself may be administered to mimic the effect of normal MIP-99 and bind c-Myc, thereby preventing its cancer causing function. These compositions may contain a pharmaceutically acceptable carrier. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

Still another method involves the use of the MIP-99 polynucleotide sequences for gene therapy. In the method, the MIP-99 sequences are introduced into a suitable vector for delivery to a cell containing a deficiency of MIP-99 and/or to block tumor growth. By conventional genetic engineering techniques, the MIP-99 gene sequence may be introduced to mutate the existing gene by recombination or to replace an inactive or missing gene.

The dose, timing and mode of administration of these compositions may be determined by one of skill in the art. Such factors as the age, condition, and the level of the MIP-99 deficiency detected by the diagnostic methods described above, may be taken into account in determining the dose, timing and mode of administration of the therapeutic compositions of the invention. Generally, where treatment of an existing cancer or hyperplastic state is indicated, a therapeutic composition of the invention is preferably administered in a site-directed manner and is repeated as needed. Such therapy may be administered in conjunction with conventional therapies, including radiation and/or chemotherapeutic treatments.

The following examples illustrate the isolation and use of the MIP99 sequences of the invention. These examples are illustrative only and do not limit the scope of the invention.

EXAMPLE 1

Identification and Characterization of MIP 99

A. Murine MIP99 cDNA

A yeast two hybrid approach [Fields, S. and O. Song., *Nature*, 340:245–6 (1989)] was used to screen for Myc-interacting proteins (MIPs) in a murine embryonic cDNA library. The cDNA library was derived from day 10.5 mouse embryonic RNA [A. B. Vojtek et al, *Cell*, 74:205–214 (1993)]. This system takes advantage of the modular nature of transcription factors, whose DNA-binding and transcriptional activating components can be assembled in trans by interacting protein (IP) domains derived from other polypeptides. A previously described two hybrid system [Vojtek et al, cited above] and a 16 amino acid nontransactivating polypeptide derived from the human c-Myc "Myc box 1" (MB1) region [Prendergast, G. C. and E. B. Ziff, *Trends in Genet.*, 8:91–96.3 (1992)] EDIWKKFELLPTPPLS (human c-Myc amino acids 47–62) [SEQ ID NO:5], were used as "bait" in the screen.

Briefly, the "bait" plasmid contained a TRP1 marker and a LexA-MB1 fusion protein as the DNA binding component, and the cDNA library plasmid contained a LEU2 marker and the herpes simplex virus VP16 protein as the transcriptional transactivator fused to the cDNA library inserts. The yeast strain L40 (MATa trp1-901 leu2-3,112 LYS2::(lexAop)4-HIS3 URA3::(lexAop)8-lacZ) served as the host for the two hybrid screen [see, Vojtek et al, cited above].

An L40 derivative expressing the MB1 "bait" was transfected with the cDNA library and TRP+LEU+ cells were selected for a HIS+LacZ+ phenotype, which is diagnostic for interaction between the "bait" and library components [Vojtek et al, cited above]. Ninety-eight of $7 \times 10^7$ independent yeast clones exhibited phenotypes consistent with interaction. The clones were cured of the original "bait" plasmid by standard methods [Guthrie, C. and G. R. Fink, eds., *Guide to Yeast Genetics and Molecular Biology*, *Meth. Enzymol.*, 194, Academic Press: New York (1991)] and the library plasmid was rescreened against a panel of test "baits" by a mating assay approach.

The test "baits" included the original MB1 peptide, a mutant MB1 peptide, a similar sized but nonspecific peptide derived from protein kinase C, and lamin. The protein kinase C peptide contained a phosphorylation site structurally analogous to the MB1 T58 phosphorylation site, which is recognized by glycogen synthase kinase-3 (GSK-3), a kinase present in yeast. The PKC peptide was designed to control for binding proteins that might nonspecificly interact with phosphooligopeptides (e.g., peptidases, kinases, phosphatases). MB1 specificity was reproducibly exhibited by 14/99 of the original yeast clones.

cDNA library plasmids were shuttled from the desired clones to *E. coli* [Guthrie et al, cited above] and the DNA sequence of the inserts was determined. All clones contained related or identical sequences of approximately 0.4 kb containing an open reading frame (ORF) of 135 amino acids encoding a Myc-interacting polypeptide, termed MIP99 [SEQ ID NO:2] exhibited specificity for Myc in two hybrid and in vitro binding assays.

B. Bacterial Expression of Murine MIP99 Polypeptide [SEQ ID NO:2] as a Soluble GST Fusion Protein To study the association of the 135 aa murine MIP polypeptide [SEQ ID NO:2] with Myc in vitro, the ~0.4 kb cDNA [SEQ ID NO:1] was expressed as a glutathione-S-transferase (GST) fusion protein and used in binding assays with $^{35}$S-methionine-labeled in vitro translated (IVT) proteins. The binding experiments were configured essentially as described in A. K. Rustgi et al, *Nature*, 352:541–544 (1991).

GST and GST-99 were purified from IPTG-induced cells by standard methods (Pharmacia). Twenty (20) µl (~0.5 µg) of purified protein was analyzed on an SDS-PA gel fixed and stained with Coomassie Blue. The apparent molecular weight (MW) of the MIP99 component of the fusion (22 kD) is larger than the predicted MW (14 kD) but is consistent with the apparent MW of in vitro translated murine MIP-99 [SEQ ID NO:2].

C. In Vitro Association of Myc and MIP 99 [SEQ ID NO:2]

Ten µl (~0.2 µg) of GST or GST-99 Sepharose slurry was incubated 1 hour at 4° C. with IVT [$^{35}$S]-Myc or Max proteins [26], washed 5 times in binding buffer (20 mM TrisCl pH 8/250 mM NaCl/0.25% NP40), and the bound fraction analyzed by SDS-PAGE/fluorography (IVT only is 1/10th volume). IVT reactions programmed by empty vectors produced essentially no signal.

D. Association of MIP99 [SEQ ID NO:2] with TBP but not USF

[$^{35}$S]-labeled TBP and USF were generated by IVT and tested for GST-99 binding as in C. above. Reinforcing the notion that it might be involved in MB1 function in transcriptional regulation, MIP99 bound to TATA-binding protein [TBP, a critical component of the basal transcription apparatus] but not to Max, the Myc-related b/HLH/LZ protein upstream stimulating factor (USF, a transcription factor), or other negative control proteins, including cell cycle protein p107, transcription factor YY1, extracellular protein PAI-1, and small GTP-binding protein RhoB.

EXAMPLE 2

Isolation of Human MIP99

BLAST searches of the dbEST DNA sequence database [GenBank] with the murine MIP-99 sequence revealed an approximately 89% identity to an 289 bp uncharacterized human "expressed sequence tag".

Northern analysis of RNA from several human tissues using a murine MIP99 cDNA [SEQ ID NO:1] as probe revealed a single RNA species of ~2.2 kb that was abundant in skeletal tissue. A 1.95 kilobase human MIP99 cDNA was obtained from a skeletal muscle lambda phage cDNA library (Stratagene, La Jolla Calif.) by standard methods [Sambrook et al, cited above], using the murine MIP 99 probe. The complete sequence of this ~2.0 kb full-length cDNA was determined [SEQ ID NO:3]. It contained a 451 amino acid ORF with high similarity in a C-terminal region to murine MIP 99. The human ORF was therefore designated human MIP99 [SEQ ID NO:4].

Characterization of the longer human MIP99 cDNA indicated that the ~0.5 kb murine ORF was conserved and embedded in a longer human ORF. Thus, the 135 aa murine MIP 99 polypeptide acts in a dominant inhibitory (DI) manner if overexpressed in vivo.

Genomic clones of human MIP99 have been obtained and are currently being characterized to map the mutations seen in hepatocarcinoma DNA.

EXAMPLE 3

Expression of Partial Murine MIP 99

This example demonstrates that the partial murine MIP-99 [SEQ ID NO:1] is a DI gene. When expressed, the partial murine MIP-99 [SEQ ID NO:2] protein augments Myc-dependent rat embryo fibroblast (REF) cell activity.

The ~0.5 kb murine cDNA [SEQ ID NO:1] was engineered with a 5' Kozak initiator methionine and subcloned into pcDNA3 (a CMV enhancer/promoter vaccine [InVitrogen, SanDiego, Calif.] to generate neoCMV-ATG99. Secondary passage rat embryo fibroblast REFs cells were seeded and transfected [G. C. Prendergast et al, *Genes Dev.*, 6:2429–2439 (1992)] with equimolar amounts of neoCMV-ATG99 and activated myc [LTR Hmyc, A. Kelekar and M. D. Cole, *Mol. Cell. Biol.*, 7:3899–3907 (1987)] and ras [pT22, human H-ras$^{V12}$ oncogene, C. Shih and R. Weinberg, *Cell*, 29:161–169 (1982)] vectors, or the control constructs pcDNA3, which is an empty plasmid vector and LTR Hmyc/Bst, which is same as LTR Hmyc except for a frameshift mutation which causes truncation at aa 104 and elimination of biological function. Total DNA in each transfection was 30 µg.

Transformed cell foci were scored 12 days post-transfection. Cells transfected with neoCMV-ATG99 exhibited a 2- to 4-fold greater number of transformed foci relative to REFs transfected only with myc and ras. The disabling c-myc frameshift mutant eliminated all foci formation activity, indicating that the augmentative effect of neoCMV-ATG99 on cell transformation was Myc-dependent. This data indicates that the Myc-MIP99 association is physiological and has negative regulatory consequences for Myc activity.

EXAMPLE 4

Expression of Human MIP99

The following example demonstrates that the expression of human MIP99 [SEQ ID NO:2] inhibits Myc-dependent rat embryo (REF) cotransforming activity.

An ~1.6 kb Eco RI restriction fragment from the human cDNA [SEQ ID NO:3] encoding the entire MIP99 polypeptide was subcloned into pcDNA3 [a cytomegalovirus enhancer/promoter expression plasmid (Invitrogen, San Diego Calif.)] to generate $CMV_3 99fE$. Secondary passage REF cells were seeded and transfected [G. C. Prendergast et al, *Genes Dev.*, 6:2429–2439 (1992)] with equimolar amounts of $CMV_3 99fE$ and activated c-myc [LTR Hmyc, A. Kelekar and M. D. Cole, *Mol. Cell. Biol.*, 7:3899–3907 (1987)] and ras [pT22, human H-ras$^{V12}$ oncogene, C. Shih and R. A. Weinberg, *Cell*, 29:161–169 (1982)] vectors, or the control constructs pcDNA3, which is an empty plasmid vector, and LTR Hmyc/Bst, which is the same as LTR Hmyc except for a frameshift mutation which causes truncation at aa 104 and loss of biological function. Total DNA in each transfection was 30 μg.

Transformed cell foci were scored 12 days post-transfection. The disabling c-myc frameshift mutations eliminated foci formation activity, verifying that cell transformation was Myc-dependent. Cells transfected with $CMV_3 99fE$ exhibited a ~10-fold reduction in transformed cell foci relative to REFS transfected only with myc and ras and empty pcDNA3 vectors. This result indicated that the Myc-MIP99 association is physiological and has negative regulatory consequences for Myc activity.

Thus, this data provides support for the use of a gene therapy vector to deliver and express MIP99 to block tumor growth.

EXAMPLE 5

Rearrangement and Loss of Expression of the MIP99 Gene in Liver and Breast Cancer Cells Because MIP99 had been demonstrated to inhibit Myc-dependent cell transformation, the following study was performed to determine if the MIP99 gene is mutated in human tumor cells. The initial experiment was to perform Southern analysis of the genomic DNA from a panel of human tumor cell lines including HeLa [cervix, ATCC CCL 2], SK-CO-1 [colon, ATCC HTB 39], HT-29 [colon, ATCC HTB 38], DU145 [prostate, ATCC HTB 41], PC-3 [prostate, ATCC CRL 1435], LNCaP [prostate, ATCC CRL 1740]; T24 [bladder, ATCC HTB4]; MCF7 [breast, ATCC HTB 22]; HepG2 [liver, ATCC HB 8065]; Rh-30 [myosarcoma, E. C. Douglass et al, "A specific chromosomal abnormality in rhabdosarcoma", *Cytogenet. Cell Genet.*, 45:148–155 (1987)]; Raji [lymphoma, ATCC CCL 86]. DNA from WI-38 normal diploid fibroblasts [ATCC CCL 75] was used as a source of normal DNA.

DNAs were isolated from by standard methods (Sambrook et al, cited above) and 5 μg per sample was treated with HindIII restriction endonuclease. Restricted DNA was fractionated on a 0.65% agarose gel which was denatured 2×15 minutes in 1.5M NaCl/0.5M NaOH, neutralized 2×30 minutes in 1.5M NaCl/0.5 TrisCl pH 8, and then blotted to a charged nylon membrane (Stratagene, La Jolla Calif.). The blot was crosslinked by UV irradiation and hybridized in a commercial hybridization solution with a random-primed $^{32}$P-labeled MIP99 cDNA probe according to the vendor's instructions (Amersham, Cambridge UK). The blot was washed 1×10 minutes with 2× SSC/0.1% SDS at 20° C. and then 2×10 minutes with 0.2 SSC/0.1% SDS at 65° C. before being exposed to X-ray film (DuPont, Wilmington Del.).

A single ~6.5 kb band was observed in all the genomic DNAs except for HepG2, a liver carcinoma cell line, where an additional band of ~3.5 kb was seen. Following this observation, a second Southern analysis was performed on a panel of 9 liver carcinoma cell lines, including Huh1, Huh2, HepG2 [ATCC HB8065], Hep3B [ATCC HB8064], Hep43, Hep63, HLF [ATCC CCL 199], NCH2, and NHep40 (provided by Dr. D. Simon, Medical College of Pennsylvania). Conditions were the same as above except that PstI restriction endonuclease was used.

Five bands of 2.5, 1.8, 1.5, 0.95, and 0.75 kb were observed in WI-38 normal DNA. Four of the nine liver tumor DNAs (HepG2, Hep3B, NCH2, and NHep40) exhibited an additional band of 2.9–3.3 kb. These data corroborated the previous results and indicated that MIP99 may be mutated during the development of human hepatocarcinoma.

Northern analysis on RNA isolated from the initial panel of human tumor cells, including HepG2 liver carcinoma cells, was performed to examine MIP99 expression. Total cytoplasmic RNA was purified by standard methods (Sambrook et al, cited above) and 15 μg was fractionated on a 1% formaldehyde agarose gel and blotted as described [G. C. Prendergast and M. D. Cole, *Mol. Cell. Biol.*, 9:124–134 (1989)]. A commercial Northern blot containing RNA from normal human brain, heart, kidney, lung, liver, skeletal muscle, pancreas, and placenta (Clontech, Palo Alto Calif.) was also analyzed. Using the same procedure and conditions as above, the Northern blots were hybridized with MIP99 cDNA probe, washed, and exposed to X-ray film.

A MIP99-specific ~2.2 kb RNA was observed in all tissues and cell lines except HepG2 and the breast carcinoma cell line MCF7. This result indicated that MIP99 was ubiquitously expressed and that mutation in HepG2 cells was correlated with loss of expression. This result also directly supports the utility of RT-PCR and FISH for diagnosing MIP99 loss in liver and breast cancer biopsies.

All documents cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

( A ) LENGTH: 402 base pairs
( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 1..399

( x i ) SEQUENCE DESCRIPTION: SEQ ID NO:1:

| GAG | ATC | AGA | GTG | AAC | CAT | GAG | CCA | GAG | CCG | GCC | AGT | GGG | GCC | TCA | CCC | 48 |
| Glu | Ile | Arg | Val | Asn | His | Glu | Pro | Glu | Pro | Ala | Ser | Gly | Ala | Ser | Pro | |
| 1 | | | | 5 | | | | | 10 | | | | | 15 | | |

| GGG | GCT | GCC | ATC | CCC | AAG | TCC | CCA | TCT | CAG | CCA | GCA | GAG | GCC | TCC | GAG | 96 |
| Gly | Ala | Ala | Ile | Pro | Lys | Ser | Pro | Ser | Gln | Pro | Ala | Glu | Ala | Ser | Glu | |
| | | | 20 | | | | | 25 | | | | | 30 | | | |

| GTG | GTG | GGT | GGA | GCC | CAG | GAG | CCA | GGG | GAG | ACA | GCA | GCC | AGT | GAA | GCA | 144 |
| Val | Val | Gly | Gly | Ala | Gln | Glu | Pro | Gly | Glu | Thr | Ala | Ala | Ser | Glu | Ala | |
| | | 35 | | | | | 40 | | | | | 45 | | | | |

| ACC | TCC | AGC | TCT | CTT | CCG | GCT | GTG | GTG | GTG | GAG | ACC | TTC | TCC | GCA | ACT | 192 |
| Thr | Ser | Ser | Ser | Leu | Pro | Ala | Val | Val | Val | Glu | Thr | Phe | Ser | Ala | Thr | |
| | 50 | | | | | 55 | | | | | 60 | | | | | |

| GTG | AAT | GGG | GCG | GTG | GAG | GGC | AGC | GCT | GGG | ACT | GGA | CGC | TTG | GAC | CTG | 240 |
| Val | Asn | Gly | Ala | Val | Glu | Gly | Ser | Ala | Gly | Thr | Gly | Arg | Leu | Asp | Leu | |
| 65 | | | | | 70 | | | | | 75 | | | | | 80 | |

| CCC | CCG | GGA | TTC | ATG | TTC | AAG | GTT | CAA | GCC | CAG | CAT | GAT | TAC | ACG | GCC | 288 |
| Pro | Pro | Gly | Phe | Met | Phe | Lys | Val | Gln | Ala | Gln | His | Asp | Tyr | Thr | Ala | |
| | | | | 85 | | | | | 90 | | | | | 95 | | |

| ACT | GAC | ACT | GAT | GAG | CTG | CAA | CTC | AAA | GCT | GGC | GAT | GTG | GTG | TTG | GTG | 336 |
| Thr | Asp | Thr | Asp | Glu | Leu | Gln | Leu | Lys | Ala | Gly | Asp | Val | Val | Leu | Val | |
| | | | 100 | | | | | 105 | | | | | 110 | | | |

| ATT | CCT | TTC | CAG | AAC | CCA | GAG | GAG | CAG | GAT | GAA | GGC | TGG | CTC | ATG | GGT | 384 |
| Ile | Pro | Phe | Gln | Asn | Pro | Glu | Glu | Gln | Asp | Glu | Gly | Trp | Leu | Met | Gly | |
| | | 115 | | | | | 120 | | | | | 125 | | | | |

| GTG | AAG | GAG | AGC | GAC | TGA | | | | | | | | | | | 402 |
| Val | Lys | Glu | Ser | Asp | | | | | | | | | | | | |
| 130 | | | | | | | | | | | | | | | | |

( 2 ) INFORMATION FOR SEQ ID NO:2:

( i ) SEQUENCE CHARACTERISTICS:
( A ) LENGTH: 133 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Glu | Ile | Arg | Val | Asn | His | Glu | Pro | Glu | Pro | Ala | Ser | Gly | Ala | Ser | Pro |
| 1 | | | | 5 | | | | | 10 | | | | | 15 | |

| Gly | Ala | Ala | Ile | Pro | Lys | Ser | Pro | Ser | Gln | Pro | Ala | Glu | Ala | Ser | Glu |
| | | | 20 | | | | | 25 | | | | | 30 | | |

| Val | Val | Gly | Gly | Ala | Gln | Glu | Pro | Gly | Glu | Thr | Ala | Ala | Ser | Glu | Ala |
| | | 35 | | | | | 40 | | | | | 45 | | | |

| Thr | Ser | Ser | Ser | Leu | Pro | Ala | Val | Val | Val | Glu | Thr | Phe | Ser | Ala | Thr |
| | 50 | | | | | 55 | | | | | 60 | | | | |

| Val | Asn | Gly | Ala | Val | Glu | Gly | Ser | Ala | Gly | Thr | Gly | Arg | Leu | Asp | Leu |
| 65 | | | | | 70 | | | | | 75 | | | | | 80 |

| Pro | Pro | Gly | Phe | Met | Phe | Lys | Val | Gln | Ala | Gln | His | Asp | Tyr | Thr | Ala |
| | | | | 85 | | | | | 90 | | | | | 95 | |

| Thr | Asp | Thr | Asp | Glu | Leu | Gln | Leu | Lys | Ala | Gly | Asp | Val | Val | Leu | Val |

|   |   |   |   |   | 100 |   |   |   |   | 105 |   |   |   |   | 110 |   |   |
|---|---|---|---|---|---|---|---|---|---|---|---|---|---|---|---|---|---|
| Ile | Pro | Phe | Gln | Asn | Pro | Glu | Glu | Gln | Asp | Glu | Gly | Trp | Leu | Met | Gly |   |   |
|   |   | 115 |   |   |   |   | 120 |   |   |   |   | 125 |   |   |   |   |   |

Val Lys Glu Ser Asp
130

( 2 ) INFORMATION FOR SEQ ID NO:3:

( i ) SEQUENCE CHARACTERISTICS:
        ( A ) LENGTH: 1925 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 60..1412

( x i ) SEQUENCE DESCRIPTION: SEQ ID NO:3:

GAATTCCGTG CTGGTTGAGC TTGCTCATCT CCTTGTGGAA GTTTTCCTCC AGGCCCGCG    59

| ATG | CTC | TGG | AAC | GTG | GTG | ACG | GCG | GGA | AAG | ATC | GCC | AGC | AAC | GTG | CAG | 107 |
|---|---|---|---|---|---|---|---|---|---|---|---|---|---|---|---|---|
| Met | Leu | Trp | Asn | Val | Val | Thr | Ala | Gly | Lys | Ile | Ala | Ser | Asn | Val | Gln |   |
| 1 |   |   |   | 5 |   |   |   |   | 10 |   |   |   |   | 15 |   |   |

| AAG | AAG | CTC | ACC | CGC | GCG | CAG | GAG | AAG | GTT | CTC | CAG | AAG | CTG | GGG | AAG | 155 |
|---|---|---|---|---|---|---|---|---|---|---|---|---|---|---|---|---|
| Lys | Lys | Leu | Thr | Arg | Ala | Gln | Glu | Lys | Val | Leu | Gln | Lys | Leu | Gly | Lys |   |
|   |   |   | 20 |   |   |   |   | 25 |   |   |   |   | 30 |   |   |   |

| GCA | GAT | GAG | ACC | AAG | GAT | GAG | CAG | TTT | GAG | CAG | TGC | GTC | CAG | AAT | TTC | 203 |
|---|---|---|---|---|---|---|---|---|---|---|---|---|---|---|---|---|
| Ala | Asp | Glu | Thr | Lys | Asp | Glu | Gln | Phe | Glu | Gln | Cys | Val | Gln | Asn | Phe |   |
|   |   | 35 |   |   |   |   | 40 |   |   |   |   | 45 |   |   |   |   |

| AAC | AAG | CAG | CTG | ACG | GAG | GGC | ACC | CGG | CTG | CAG | AAG | GAT | CTC | CGG | ACC | 251 |
|---|---|---|---|---|---|---|---|---|---|---|---|---|---|---|---|---|
| Asn | Lys | Gln | Leu | Thr | Glu | Gly | Thr | Arg | Leu | Gln | Lys | Asp | Leu | Arg | Thr |   |
|   | 50 |   |   |   |   | 55 |   |   |   |   | 60 |   |   |   |   |   |

| TAC | CTG | GCC | TCC | GTC | AAA | GCC | ATG | CAC | GAG | GCT | TCC | AAG | AAG | CTG | AAT | 299 |
|---|---|---|---|---|---|---|---|---|---|---|---|---|---|---|---|---|
| Tyr | Leu | Ala | Ser | Val | Lys | Ala | Met | His | Glu | Ala | Ser | Lys | Lys | Leu | Asn |   |
| 65 |   |   |   |   | 70 |   |   |   |   | 75 |   |   |   |   | 80 |   |

| GAG | TGT | CTG | CAG | GAG | GTG | TAT | GAG | CCC | GAT | TGG | CCC | GGC | AGG | GAT | GAG | 347 |
|---|---|---|---|---|---|---|---|---|---|---|---|---|---|---|---|---|
| Glu | Cys | Leu | Gln | Glu | Val | Tyr | Glu | Pro | Asp | Trp | Pro | Gly | Arg | Asp | Glu |   |
|   |   |   |   | 85 |   |   |   |   | 90 |   |   |   |   | 95 |   |   |

| GCA | AAC | AAG | ATC | GCA | GAG | AAC | AAC | GAC | CTG | CTG | TGG | ATG | GAT | TAC | CAC | 395 |
|---|---|---|---|---|---|---|---|---|---|---|---|---|---|---|---|---|
| Ala | Asn | Lys | Ile | Ala | Glu | Asn | Asn | Asp | Leu | Leu | Trp | Met | Asp | Tyr | His |   |
|   |   |   | 100 |   |   |   |   | 105 |   |   |   |   | 110 |   |   |   |

| CAG | AAG | CTG | GTG | GAC | CAG | GCG | CTG | CTG | ACC | ATG | GAC | ACG | TAC | CTG | GGC | 443 |
|---|---|---|---|---|---|---|---|---|---|---|---|---|---|---|---|---|
| Gln | Lys | Leu | Val | Asp | Gln | Ala | Leu | Leu | Thr | Met | Asp | Thr | Tyr | Leu | Gly |   |
|   |   | 115 |   |   |   |   | 120 |   |   |   |   | 125 |   |   |   |   |

| CAG | TTC | CCC | GAC | ATC | AAG | TCA | CGC | ATT | GCC | AAG | CGG | GGG | CGC | AAG | CTG | 491 |
|---|---|---|---|---|---|---|---|---|---|---|---|---|---|---|---|---|
| Gln | Phe | Pro | Asp | Ile | Lys | Ser | Arg | Ile | Ala | Lys | Arg | Gly | Arg | Lys | Leu |   |
|   | 130 |   |   |   |   | 135 |   |   |   |   | 140 |   |   |   |   |   |

| GTG | GAC | TAC | GAC | AGT | GCC | CGG | CAC | CAC | TAC | GAG | TCC | CTT | CAA | ACT | GCC | 539 |
|---|---|---|---|---|---|---|---|---|---|---|---|---|---|---|---|---|
| Val | Asp | Tyr | Asp | Ser | Ala | Arg | His | His | Tyr | Glu | Ser | Leu | Gln | Thr | Ala |   |
| 145 |   |   |   |   | 150 |   |   |   |   | 155 |   |   |   |   | 160 |   |

| AAA | AAG | AAG | GAT | GAA | GCC | AAA | ATT | GCC | AAG | GCC | GAG | GAG | GAG | CTC | ATC | 587 |
|---|---|---|---|---|---|---|---|---|---|---|---|---|---|---|---|---|
| Lys | Lys | Lys | Asp | Glu | Ala | Lys | Ile | Ala | Lys | Ala | Glu | Glu | Glu | Leu | Ile |   |
|   |   |   |   | 165 |   |   |   |   | 170 |   |   |   |   | 175 |   |   |

| AAA | GCC | CAG | AAG | GTG | TTT | GAG | GAG | ATG | AAT | GTG | GAT | CTG | CAG | GAG | GAG | 635 |
|---|---|---|---|---|---|---|---|---|---|---|---|---|---|---|---|---|
| Lys | Ala | Gln | Lys | Val | Phe | Glu | Glu | Met | Asn | Val | Asp | Leu | Gln | Glu | Glu |   |
|   |   |   | 180 |   |   |   |   | 185 |   |   |   |   | 190 |   |   |   |

| CTG | CCG | TCC | CTG | TGG | AAC | AGC | CGC | GTA | GGT | TTC | TAC | GTC | AAC | ACG | TTC | 683 |
|---|---|---|---|---|---|---|---|---|---|---|---|---|---|---|---|---|
| Leu | Pro | Ser | Leu | Trp | Asn | Ser | Arg | Val | Gly | Phe | Tyr | Val | Asn | Thr | Phe |   |
|   |   | 195 |   |   |   |   | 200 |   |   |   |   | 205 |   |   |   |   |

| CAG | AGC | ATC | GCG | GGC | CTG | GAG | GAA | AAC | TTC | CAC | AAG | GAG | ATG | AGC | AAG | 731 |
|---|---|---|---|---|---|---|---|---|---|---|---|---|---|---|---|---|

```
Gln Ser Ile Ala Gly Leu Glu Glu Asn Phe His Lys Glu Met Ser Lys
    210             215                 220

CTC AAC CAG AAC CTC AAT GAT GTG CTG GTC GGC CTG GAG AAG CAA CAC     779
Leu Asn Gln Asn Leu Asn Asp Val Leu Val Gly Leu Glu Lys Gln His
225             230                 235                 240

GGG AGC AAC ACC TTC ACG GTC AAG GCC CAG CCC AGA AAG AAA AGT AAA     827
Gly Ser Asn Thr Phe Thr Val Lys Ala Gln Pro Arg Lys Lys Ser Lys
                245                 250                 255

CTG TTT TCG CGG CTG CGC AGA AAG AAG AAC AGT GAC AAC GCG CCT GCA     875
Leu Phe Ser Arg Leu Arg Arg Lys Lys Asn Ser Asp Asn Ala Pro Ala
            260                 265                 270

AAA GGG AAC AAG AGC CCT TCG CCT CCA GAT GGC TCC CCT GCC GCC ACC     923
Lys Gly Asn Lys Ser Pro Ser Pro Pro Asp Gly Ser Pro Ala Ala Thr
        275                 280                 285

CCC GAG ATC AGA GTC AAC CAC GAG CCA GAG CCG GCC GGG GGG GCC ACG     971
Pro Glu Ile Arg Val Asn His Glu Pro Glu Pro Ala Gly Gly Ala Thr
    290                 295                 300

CCC GGG GCC ACC CTC CCC AAG TCC CCA TCT CAG CCA GCA GAG GCC TCG    1019
Pro Gly Ala Thr Leu Pro Lys Ser Pro Ser Gln Pro Ala Glu Ala Ser
305             310                 315                 320

GAG GTG GCG GGT GGG ACC CAA CCT GCG GCT GGA GCC CAG GAG CCA GGG    1067
Glu Val Ala Gly Gly Thr Gln Pro Ala Ala Gly Ala Gln Glu Pro Gly
                325                 330                 335

GAG ACT TCT GCA AGT GAA GCA GCC TCC AGC TCT CTT CCT GCT GTC GTG    1115
Glu Thr Ser Ala Ser Glu Ala Ala Ser Ser Ser Leu Pro Ala Val Val
            340                 345                 350

GTG GAG ACC TTC CCA GCA ACT GTG AAT GGC ACC GTG GAG GGC GGC AGT    1163
Val Glu Thr Phe Pro Ala Thr Val Asn Gly Thr Val Glu Gly Gly Ser
        355                 360                 365

GGG GCC GGG CGC TTG GAC CTG CCC CCA GGT TTC ATG TTC AAG GTA CAG    1211
Gly Ala Gly Arg Leu Asp Leu Pro Pro Gly Phe Met Phe Lys Val Gln
370             375                 380

GCC CAG CAC GAC TAC ACG GCC ACT GAC ACA GAC GAG CTG CAG CTC AAG    1259
Ala Gln His Asp Tyr Thr Ala Thr Asp Thr Asp Glu Leu Gln Leu Lys
385             390                 395                 400

GCT GGT GAT GTG GTG CTG GTG ATC CCC TTC CAG AAC CCT GAA GAG CAG    1307
Ala Gly Asp Val Val Leu Val Ile Pro Phe Gln Asn Pro Glu Glu Gln
                405                 410                 415

GAT GAA GGC TGG CTC ATG GGC GTG AAG GAG AGC GAC TGG AAC CAG CAC    1355
Asp Glu Gly Trp Leu Met Gly Val Lys Glu Ser Asp Trp Asn Gln His
            420                 425                 430

AAG AAG CTG GAG AAG TGC CGT GGC GTC TTC CCC GAG AAC TTC ACT GAG    1403
Lys Lys Leu Glu Lys Cys Arg Gly Val Phe Pro Glu Asn Phe Thr Glu
        435                 440                 445

AGG GTC CCA TGACGGCGGG GCCCAGGCAG CCTCCGGGCG TGTGAAGAAC            1452
Arg Val Pro
    450

ACCTCCTCCC GAAAAATGTG TGGTTCTTTT TTTTGTTTTG TTTTCGTTTT TCATCTTTTG  1512

AAGAGCAAAG GGAAATCAAG AGGAGACCCC CAGGCAGAGG GGCGTTCTCC CAAAGTTTAG  1572

GTCGTTTTCC AAAGAGCCGC GTCCCGGCAA GTCCGGCGGA ATTCACCAGT GTTCCTGAAG  1632

CTGCTGTGTC CTCTAGTTGA GTTTCTGGCG CCCCTGCCTG TGCCCGCATG TGTGCCTGGC  1692

CGCAGGGCGG GGCTGGGGGC TGCCGAGCCA CCATACTTAA CTGAAGCTTC GGCCGCACCA  1752

CCCGGGGAAG GGTCCTCTTT TCCTGGCAGC TGCTGTGGGT GGGGCCCAGA CACCAGCCTA  1812

GCCTGCTCTG CCCCGCAGAC GGTCTGTGTG CTGTTTGAAA ATAAATCTTA GTGTTCAAAA  1872

CAAAATGAAA CAAAAAAAAA AATGATAAAA ACTCTCAAAA AAACAAGGAA TTC         1925
```

(2) INFORMATION FOR SEQ ID NO:4:

(i) SEQUENCE CHARACTERISTICS:
    (A) LENGTH: 451 amino acids
    (B) TYPE: amino acid
    (D) TOPOLOGY: linear (ii) MOLECULE TYPE: protein (xi) SEQUENCE DESCRIPTION: SEQ ID NO:4:

```
Met Leu Trp Asn Val Val Thr Ala Gly Lys Ile Ala Ser Asn Val Gln
 1               5                  10                  15

Lys Lys Leu Thr Arg Ala Gln Glu Lys Val Leu Gln Lys Leu Gly Lys
            20                  25                  30

Ala Asp Glu Thr Lys Asp Glu Gln Phe Glu Gln Cys Val Gln Asn Phe
        35                  40                  45

Asn Lys Gln Leu Thr Glu Gly Thr Arg Leu Gln Lys Asp Leu Arg Thr
    50                  55                  60

Tyr Leu Ala Ser Val Lys Ala Met His Glu Ala Ser Lys Lys Leu Asn
65                  70                  75                  80

Glu Cys Leu Gln Glu Val Tyr Glu Pro Asp Trp Pro Gly Arg Asp Glu
                85                  90                  95

Ala Asn Lys Ile Ala Glu Asn Asn Asp Leu Leu Trp Met Asp Tyr His
            100                 105                 110

Gln Lys Leu Val Asp Gln Ala Leu Leu Thr Met Asp Thr Tyr Leu Gly
        115                 120                 125

Gln Phe Pro Asp Ile Lys Ser Arg Ile Ala Lys Arg Gly Arg Lys Leu
    130                 135                 140

Val Asp Tyr Asp Ser Ala Arg His His Tyr Glu Ser Leu Gln Thr Ala
145                 150                 155                 160

Lys Lys Lys Asp Glu Ala Lys Ile Ala Lys Ala Glu Glu Glu Leu Ile
                165                 170                 175

Lys Ala Gln Lys Val Phe Glu Glu Met Asn Val Asp Leu Gln Glu Glu
            180                 185                 190

Leu Pro Ser Leu Trp Asn Ser Arg Val Gly Phe Tyr Val Asn Thr Phe
        195                 200                 205

Gln Ser Ile Ala Gly Leu Glu Glu Asn Phe His Lys Glu Met Ser Lys
    210                 215                 220

Leu Asn Gln Asn Leu Asn Asp Val Leu Val Gly Leu Glu Lys Gln His
225                 230                 235                 240

Gly Ser Asn Thr Phe Thr Val Lys Ala Gln Pro Arg Lys Lys Ser Lys
                245                 250                 255

Leu Phe Ser Arg Leu Arg Arg Lys Lys Asn Ser Asp Asn Ala Pro Ala
            260                 265                 270

Lys Gly Asn Lys Ser Pro Ser Pro Pro Asp Gly Ser Pro Ala Ala Thr
        275                 280                 285

Pro Glu Ile Arg Val Asn His Glu Pro Glu Pro Ala Gly Gly Ala Thr
    290                 295                 300

Pro Gly Ala Thr Leu Pro Lys Ser Pro Ser Gln Pro Ala Glu Ala Ser
305                 310                 315                 320

Glu Val Ala Gly Gly Thr Gln Pro Ala Ala Gly Ala Gln Glu Pro Gly
                325                 330                 335

Glu Thr Ser Ala Ser Glu Ala Ala Ser Ser Ser Leu Pro Ala Val Val
            340                 345                 350

Val Glu Thr Phe Pro Ala Thr Val Asn Gly Thr Val Glu Gly Gly Ser
        355                 360                 365
```

| | | | | | | | | | | | | | | |
|---|---|---|---|---|---|---|---|---|---|---|---|---|---|---|
| Gly | Ala<br>370 | Gly | Arg | Leu | Asp | Leu<br>375 | Pro | Pro | Gly | Phe | Met<br>380 | Phe | Lys | Val | Gln |
| Ala<br>385 | Gln | His | Asp | Tyr | Thr<br>390 | Ala | Thr | Asp | Thr | Asp<br>395 | Glu | Leu | Gln | Leu | Lys<br>400 |
| Ala | Gly | Asp | Val | Val<br>405 | Leu | Val | Ile | Pro | Phe<br>410 | Gln | Asn | Pro | Glu | Glu<br>415 | Gln |
| Asp | Glu | Gly | Trp<br>420 | Leu | Met | Gly | Val | Lys<br>425 | Glu | Ser | Asp | Trp | Asn<br>430 | Gln | His |
| Lys | Lys | Leu<br>435 | Glu | Lys | Cys | Arg | Gly<br>440 | Val | Phe | Pro | Glu | Asn<br>445 | Phe | Thr | Glu |
| Arg | Val<br>450 | Pro | | | | | | | | | | | | | |

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:5:

| | | | | | | | | | | | | | | |
|---|---|---|---|---|---|---|---|---|---|---|---|---|---|---|
| Glu<br>1 | Asp | Ile | Trp | Lys<br>5 | Lys | Phe | Glu | Leu | Leu<br>10 | Pro | Thr | Pro | Pro | Leu<br>15 | Ser |

What is claimed is:

1. An isolated nucleic acid sequence selected from the group consisting of:
   a) SEQ ID NO:1; and
   b) a sequence comprising 400 nucleotides which hybridizes to SEQ ID NO:1 under stringent conditions.

2. An isolated nucleic acid sequence selected from the group consisting of:
   a) SEQ ID NO:3; and
   b) a sequence comprising 400 nucleotides which hybridizes to SEQ ID NO:3 under stringent conditions.

3. The isolated nucleic acid sequence according to claim 1 which encodes murine MIP SEQ ID NO:2.

4. The isolated nucleic acid sequence according to claim 2 which encodes human MIP SEQ ID NO:4.

5. The isolated nucleic acid sequence according to claim 1 consisting of SEQ ID NO:1.

6. The isolated nucleic acid sequence according to claim 2 consisting of SEQ ID NO:3.

7. A vector comprising a mammalian nucleic acid sequence encoding a c-myc interacting polypeptide (MIP) under the control of suitable regulatory sequences, said mammalian nucleic acid sequence selected from the group consisting of:
   a) SEQ ID NO:1;
   b) SEQ ID NO:3;
   c) a sequence comprising 400 nucleotides which hybridizes to SEQ ID NO:1 under stringent conditions; and
   d) a sequence comprising 400 nucleotides which hybridizes to SEQ ID NO:3 under stringent conditions.

8. A host cell transformed with the vector according to claim 7.

\* \* \* \* \*